(12) United States Patent
Anguillesi et al.

(10) Patent No.: US 7,146,868 B2
(45) Date of Patent: Dec. 12, 2006

(54) MACHINE AND PROCESS FOR CARRYING OUT QUICK TESTS ON TEXTILE MATERIALS FOR ACCESSING COLOR FASTNESS AND/OR ABILITY TO BE DYED THEREOF

(75) Inventors: Mauro Anguillesi, Prato (IT); Moreno Bartalucci, S. Gimignano (IT); Mario Scatizzi, Pistoia (IT)

(73) Assignee: Tecnorama, S.R.L.

( * ) Notice: Subject to any disclaimer, the term of this patent is extended or adjusted under 35 U.S.C. 154(b) by 166 days.

(21) Appl. No.: 10/780,222

(22) Filed: Feb. 17, 2004

(65) Prior Publication Data
US 2004/0177682 A1    Sep. 16, 2004

(30) Foreign Application Priority Data
Feb. 18, 2003   (IT)  ............................ FI2003A0041

(51) Int. Cl.
*G01N 33/36*       (2006.01)
(52) U.S. Cl. ..................................... 73/865.6; 866/159
(58) Field of Classification Search ................ 73/865.6, 73/159, 866
See application file for complete search history.

(56) References Cited

U.S. PATENT DOCUMENTS

| | | | | | |
|---|---|---|---|---|---|
| 2,630,710 | A | * | 3/1953 | Millson et al. ................ | 73/159 |
| 4,012,954 | A | * | 3/1977 | Klippert ..................... | 73/865.6 |
| 4,817,447 | A | * | 4/1989 | Kashima et al. ........... | 73/865.6 |
| 4,995,273 | A | * | 2/1991 | Kisima et al. ............. | 73/865.6 |
| 5,226,318 | A | * | 7/1993 | Huber et al. ................. | 73/159 |
| 6,662,635 | B1 | * | 12/2003 | Mansky ....................... | 73/159 |

FOREIGN PATENT DOCUMENTS

| JP | 58021164 A | * | 2/1983 |
|---|---|---|---|
| JP | 58088659 A | * | 5/1983 |
| JP | 63070164 A | * | 3/1988 |

* cited by examiner

Primary Examiner—Hezron Williams
Assistant Examiner—Nashmiya Fayyaz
(74) Attorney, Agent, or Firm—McGlew & Tuttle, PC

(57) ABSTRACT

A plate (1) supports a sample of the material under test, and a clamp or compressor (2; 7; 72) compresses the sample and a multifibre witness or fabric standard (4) on the plate (1). The plate (1) defines a plurality of through holes (12) associated with an injection system (5) for injecting one or more liquids through the holes (12).

14 Claims, 7 Drawing Sheets

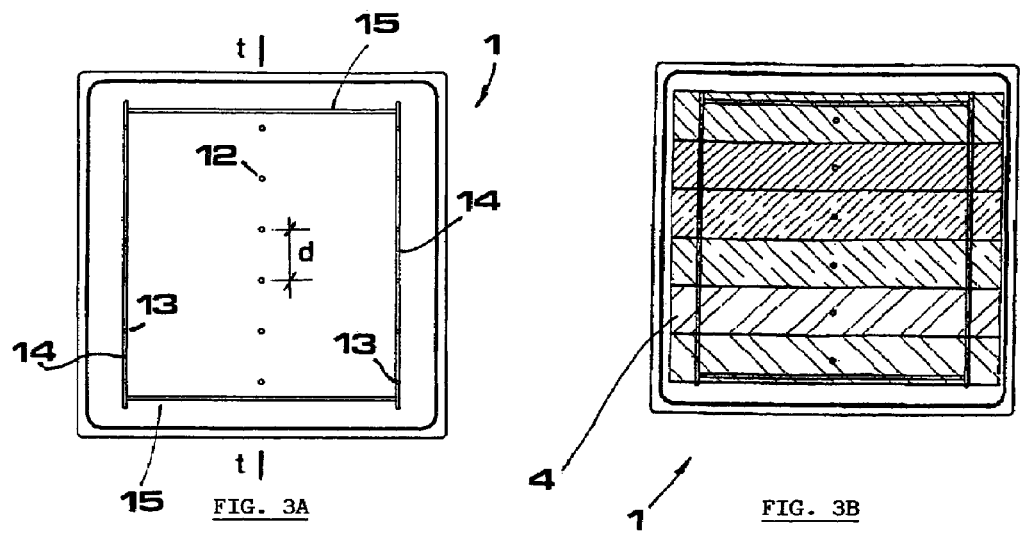
FIG. 3A
FIG. 3B
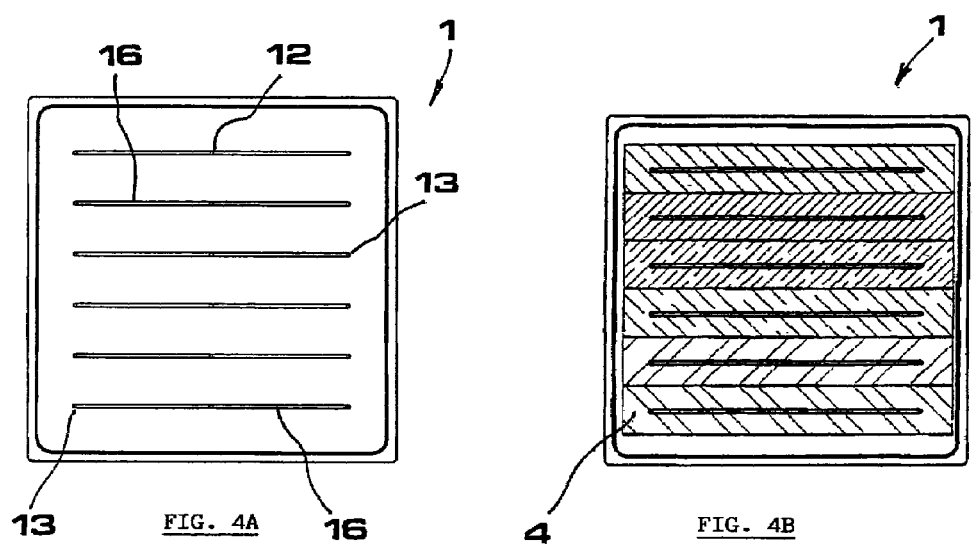
FIG. 4A
FIG. 4B
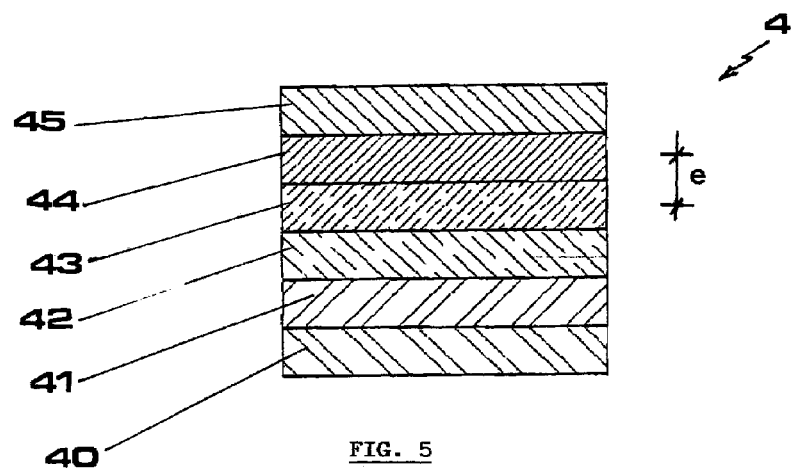
FIG. 5

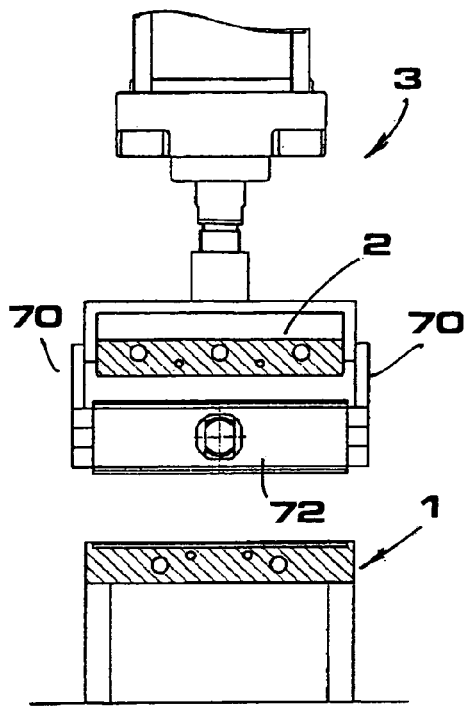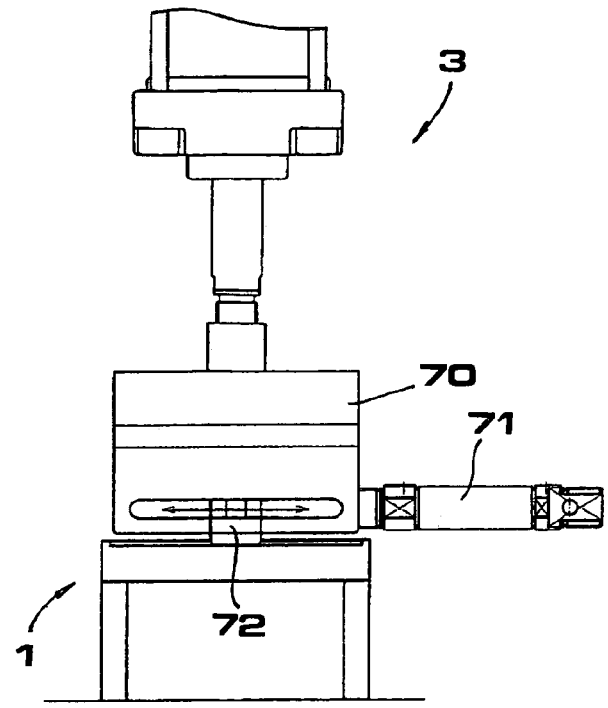
FIG. 8A     FIG. 8B
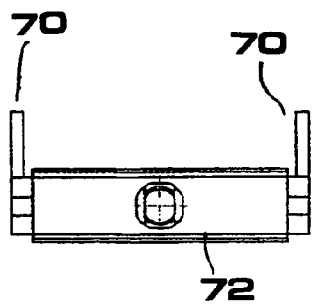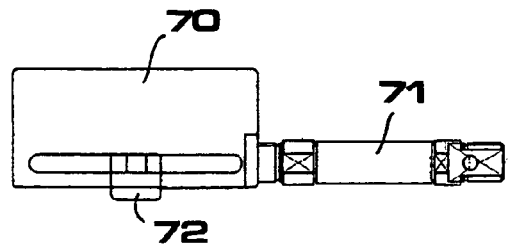
FIG. 9A     FIG. 9B

MACHINE AND PROCESS FOR CARRYING OUT QUICK TESTS ON TEXTILE MATERIALS FOR ACCESSING COLOR FASTNESS AND/OR ABILITY TO BE DYED THEREOF

FIELD OF THE INVENTION

The present invention refers to a machine and a process for carrying out quick tests on textile materials for accessing their colour fastness and/or ability to be dyed.

BACKGROUND OF THE INVENTION

A process for dyeing textile materials is known to usually include a step of checking the color fastness thereof. Such inspection should be performed before unloading the materials from the machines in which the dyeing is carried out, in order to subject the materials, in case of unfavourable outcome, to a washing or cleaning treatment. During this step, in fact, it may be economically more advantageous to reprocess the materials than unloading them and classifying or selling them as second-rate or defective products.

SUMMARY AND OBJECTS OF THE INVENTION

The main object of the present invention is to propose a machine and a process which allow carrying out tests or checks over colour fastness with maximum rapidity and reliability.

This result has been achieved, according to the invention, by by adopting the idea of making a machine and providing a process having the characteristics disclosed in the independent claims. Further characteristics being set forth in the dependent claims.

This invention makes it possible to perform tests of colour fastness on dyed textiles, as well as tests for accessing their ability to be dyed, with maximum rapidity and extreme accuracy. Moreover, a machine according to the invention is easy to make, cost-effective and reliable even after a prolonged service life.

These and other advantages and characteristics of the invention will be best understood by anyone skilled in the art from a reading of the following description in conjunction with the attached drawings given as a practical exemplification of the invention, but not to be considered in a limitative sense.

BRIEF DESCRIPTION OF THE DRAWINGS

FIG. 3A is a plan view of the lower plate;

FIG. 3B shows the same plate as FIG. 3A with a witness or fabric standard disposed thereon for carrying out a test;

FIG. 4A is a plan view of an alternative embodiment of the lower plate according to the invention;

FIG. 4B shows the same plate as FIG. 4A with a witness disposed thereon for carrying out a test;

FIG. 5 is a plan view of a witness;

FIG. 8A is a front view of a further embodiment of the machine according to the invention;

FIG. 8B is a side view of the machine of FIG. 8A;

FIG. 9A shows an enlarged detail of the drawing of FIG. 8A;

FIG. 9B shows an enlarged detail of the drawing of FIG. 8B;

DESCRIPTION OF THE PREFERRED EMBODIMENT

Figure 1:
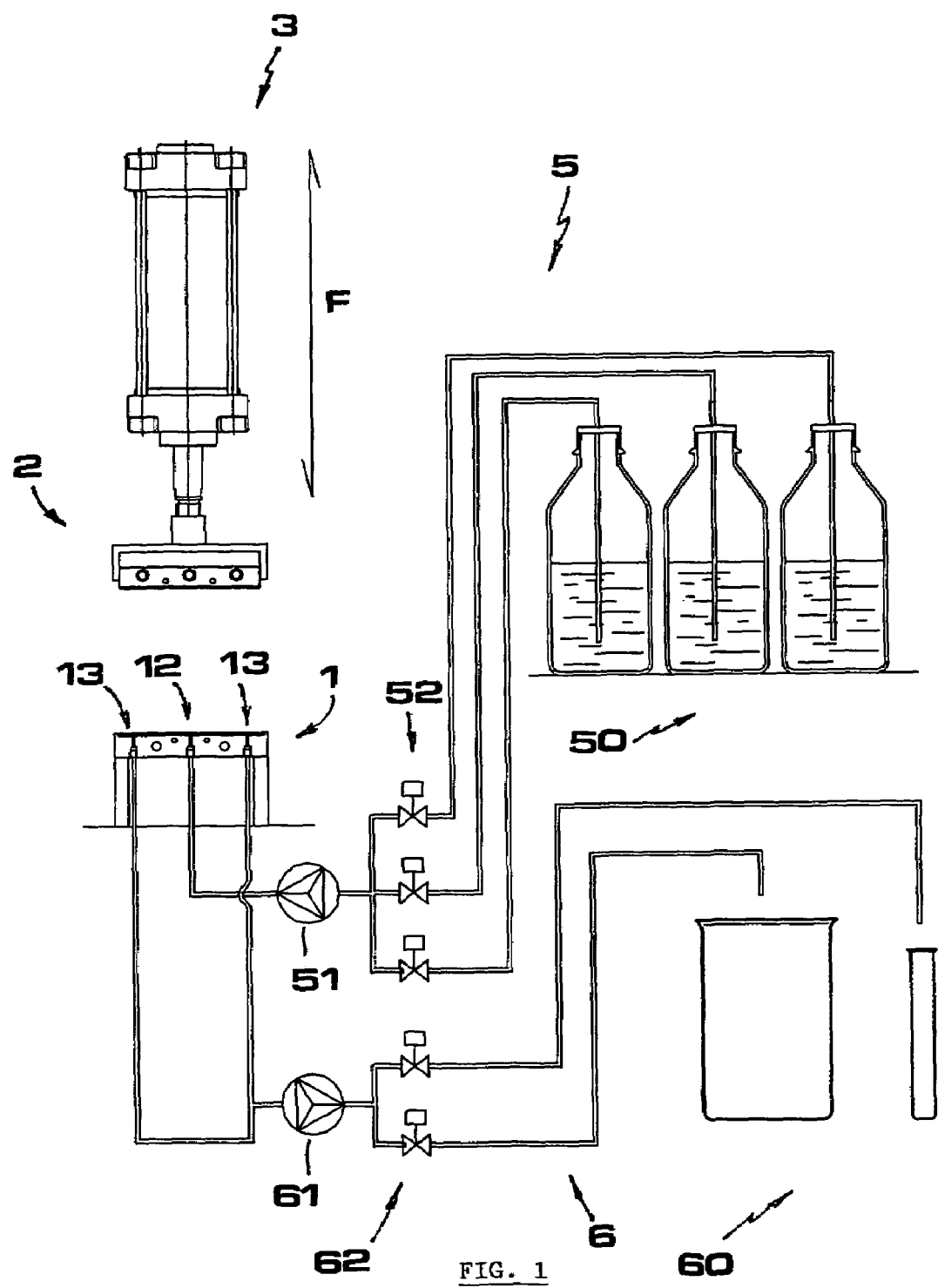
FIG. 1 shows a schematic diagram of a plant including a machine according to the invention.

Reduced to its basic structure, and reference being made to the figures of the attached drawings, a machine according to the invention comprises a stationary plate (1) and above this a movable plate (2) associated with a vertical actuator (3) to allow the movement thereof from and to the stationary plate (1), as indicated by the double arrow (F) in FIG. 1. The said plate (1) and actuator (3) are positioned in a fixed support structure which is not shown in the figures of the attached drawings for the sake of simplicity.

Figure 2:
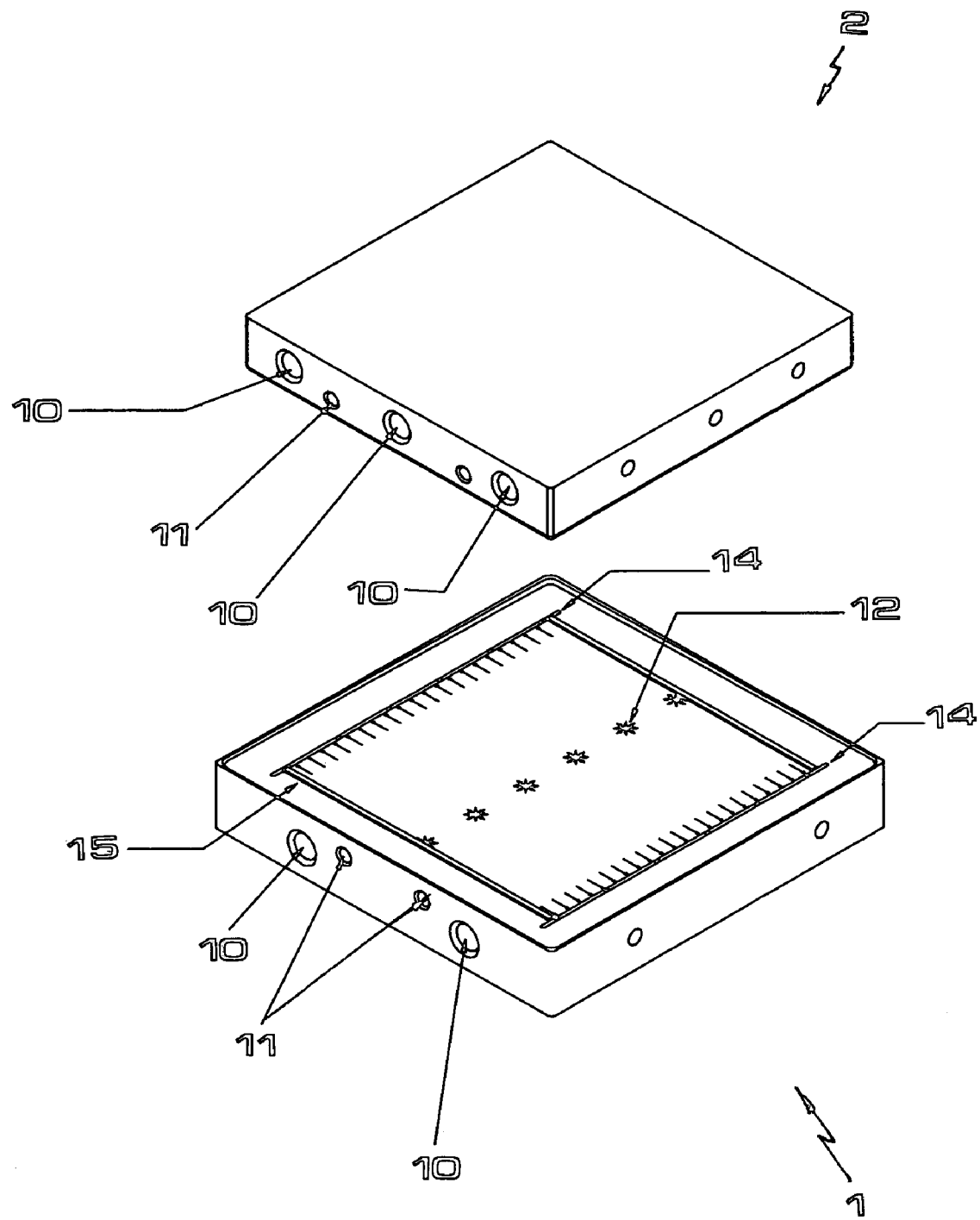
FIG. 2 is a schematic perspective view of the upper and lower plates.
Figures 6A, 6B:
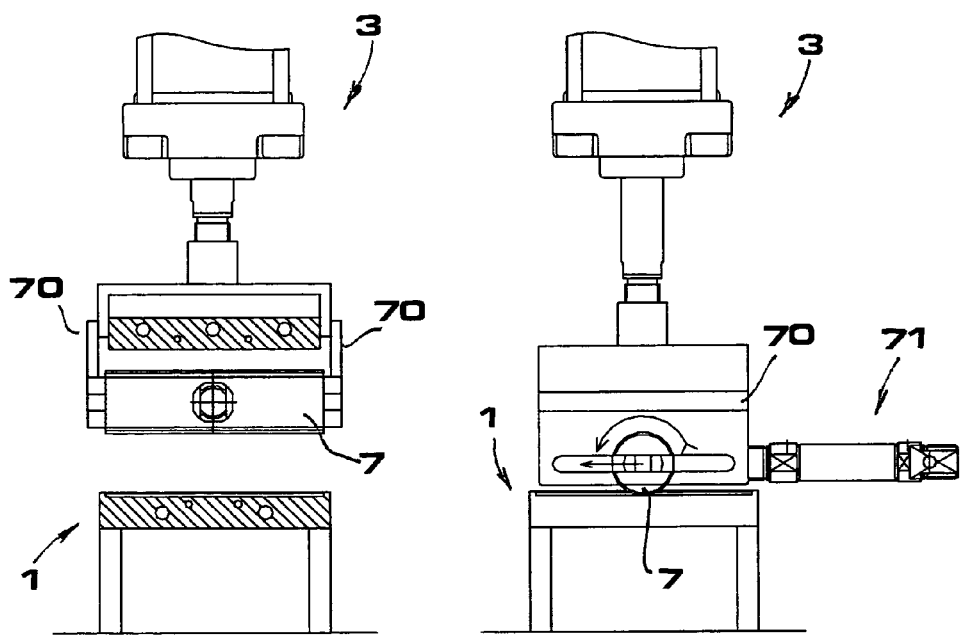
FIG. 6A is a front view of a further embodiment of the machine according to the invention.
FIG. 6B is a side view of the machine of FIG. 6A.
Figures 7A, 7B:
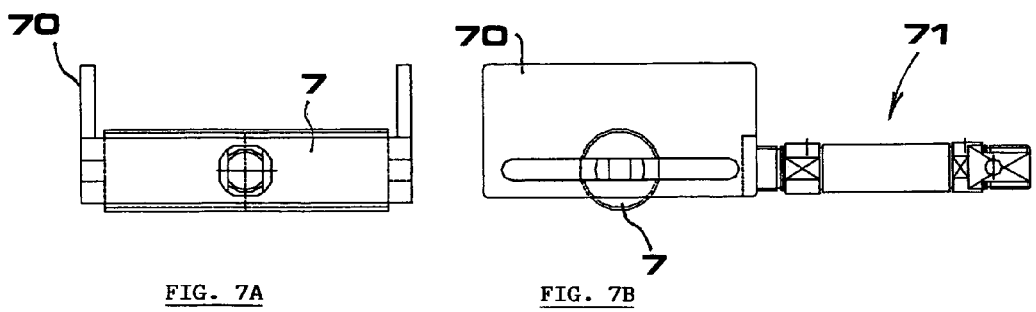
FIG. 7A shows an enlarged detail of the drawing of FIG. 6A.
FIG. 7B shows an enlarged detail of the drawing of FIG. 6B.
Figures 10A, 10B:
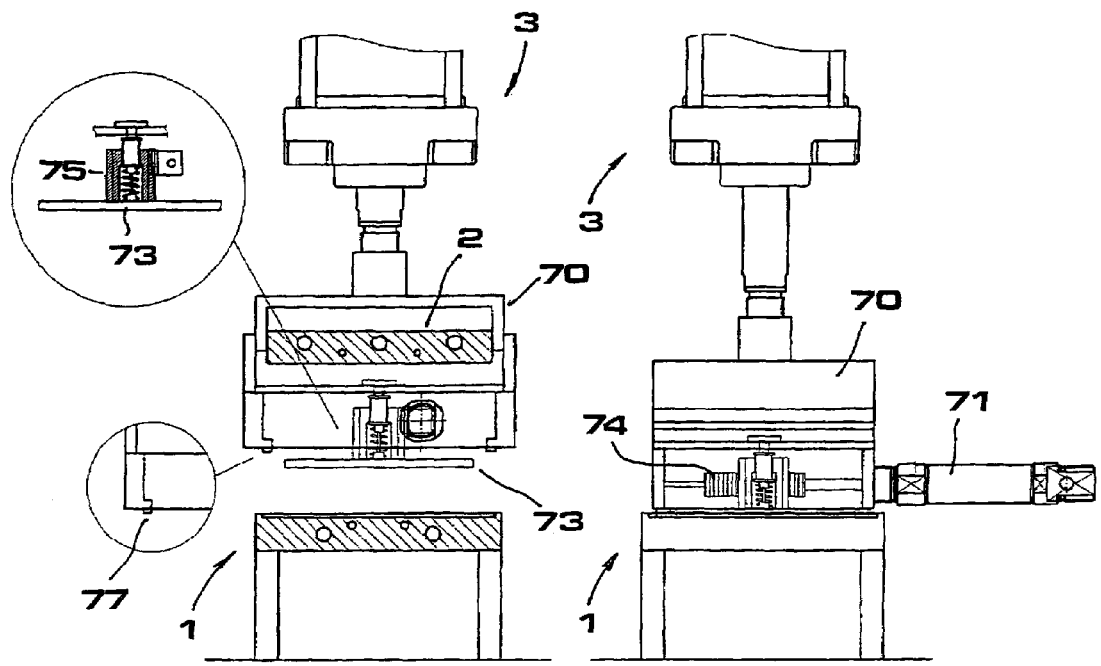
FIG. 10A is a front view of a further embodiment of the machine according to the invention.
FIG. 10B is a side view of the machine of FIG. 10A.
Figure 11B:
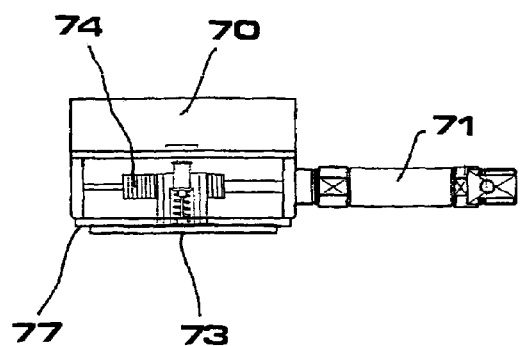
FIG. 11B shows an enlarged detail of the drawing of FIG. 10B.
Figure 11A:
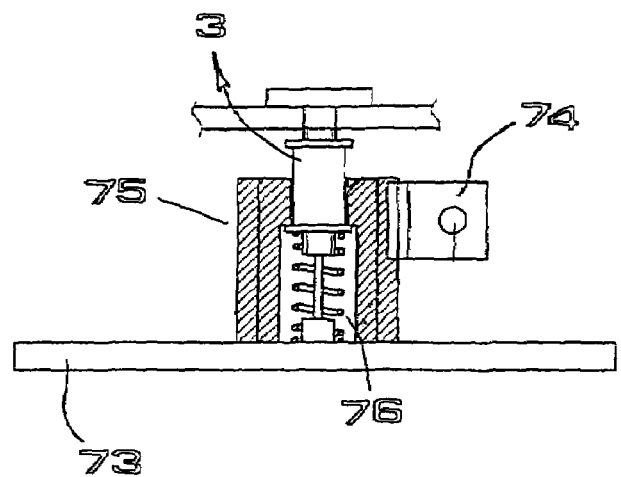
FIG. 11A shows an enlarged detail of the drawing of FIG. 10A.
Figure 11C:
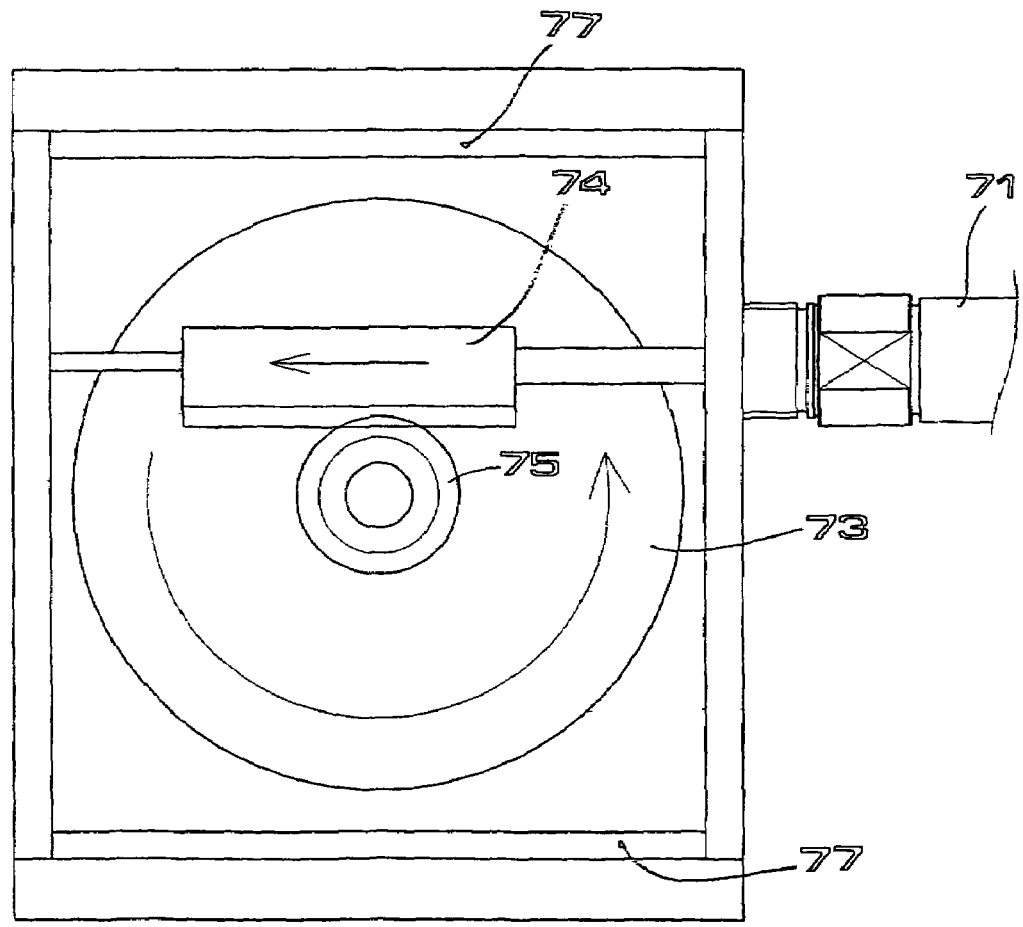
FIG. 11C shows the detail of FIG. 11 in plan view.

Both the lower (1) and upper (2) plates are able to be heated. Illustrate in FIG. 2 are seats (10, 11) for corresponding electric resistances and temperature sensors which are connectable to a programmable source of electric power to heat both plates, that is, to bring them at predetermined temperatures over time intervals to be preset as well.

Advantageously, the said plate (1) is provided with a plurality of through holes (12) which cross it from one side to the other, that is, from the upper to the lower faces thereof.

According to the example shown in the figures of the attached drawings, the said holes (12) are aligned along a central line (t—t) of plate (1) and are equidistant from each other.

In the example, the centre distance (d) between said holes (12) corresponds to the centre distance (e) between the strips of a multifibre witness (4), that is, of a ribbon-shaped fabric of known and preset width (according to specifications commonly enforced in this industrial sector, the whole witness length is about 9 cm) composed of more strips (40–45) of equal width and consisting of bundles of threads of different nature. In other words, as shown by the example of the drawings, the number of said holes (12) is equal to that of the strips (40–45) of the multifibre witness (4). The strips are made up of yarns of different nature, such as natural, artificial or synthetic fibres. For example, the strip (40) may consist of wool threads, the strip (41) of cotton threads, the strip (42) of rayon viscosa threads, the strip (43) of polyamide threads, the strip (44) of polyester threads and the strip (45) of polyacrylonitrile.

In this way, the multifibre witness (4) is formed by fibres of different materials—representing those most commonly used for the production of textiles—and orderly collected into strips adjacent to each other.

Through said holes (12) of the lower plate (1) it is possible to inject liquid substances of different nature (such as water or organic solvents) by means of a relevant circuit (5). The latter comprises a plurality of liquid-holding vessels or tanks (50) individually connected to a pump (51) via respective conduits intercepted by valves (52) which allow selecting each time one of the tanks of liquids among those available.

In addition, the said lower plate (1) exhibits two rows of discharge holes (13) located on the two sides of the central holes (12).

According to the example illustrated in FIG. 3A, each row of discharge holes (13) is within a corresponding channel-like groove (14), and two septa (15) of reduced height develop between the said groove (14) by forming two corresponding liquid-retention barriers which have the central row of injection holes (12) therebetween.

According to the example illustrated in FIG. 4A, each hole of the central row lies in a channel-shaped groove (16) which also includes two corresponding discharge holes (13) so that, within one same groove (16) the injection hole (12) will result intermediate between two discharge holes (13).

In any case, the said discharge holes (13) are associated with liquid-sucking means (6) which include a suction pump (61) connected to the holes (13) via corresponding conduits, and which provides for discharging the liquids into one or more vessels (60).

The liquid-discharging conduits are intercepted downstream of the suction pump (61) by corresponding valves (62) to allow the selection of one or the other of vessels (60) into which the liquids are to be discharged. The said plates (1, 2) may be rectangular, square or any other suitable shape.

The operation of the machine above described is as follows.

The multifibre witness (4) is positioned upon the stationary plate (1) so that each strip (40–45) thereof will result in correspondence of a hole (12). A sample of the material under test is positioned upon the multifibre witness, as illustrated in FIGS. 3B and 4B, then a command is given for lowering the upper plate (2) and heating both plates at the preset temperature. In this way, the plate (2) is caused to press the sample under test and the multifibre witness upon the lower plate (1), the test being made under known conditions of temperature and pressure. The liquids withdrawn in preset amounts by means of the pump (51) and valves (52) from one or more vessels (50) are injected through the holes (12). After a preset time interval, during which the liquids introduced through the plate (1) reach the required temperature, the pump (61) is activated for sucking the liquids previously injected and discharging them into one of the vessels (60). Upon completion of this step, the plate (2) is lifted up to allow the visual inspection of the multifibre witness (4) and, when required, of the sample. This inspection makes it possible to check the fastness of the sample's colour, that is, to check whether, and to which extent, one or more strips of the multifibre witness (4) result dyed, or in other words, whether the sample's colour results also on the fibres of one or more strips (40–45) under the test's temperature and pressure conditions. At the same time, it is possible to check whether the hue of the sample results altered. The liquids discharged into the vessels (60) can be subject to both visual and instrument-assisted examinations, such as the visual control of the colour and/or pH measurements.

The present machine makes it possible to carry out the above described test while the materials are still in the dyeing station, so that, in case of unfavourable output, it is still possible to subject the materials to washing or cleaning, instead of unloading them and subjecting them to finishing treatments which make the washing and cleaning operations substantially ineffective. As a consequence, the adoption of a machine according to the present invention allows reducing drastically the amount of dyed textiles to be classified as defective or of second rate.

According to a further embodiment, a machine according to the invention, and as represented in the FIGS. 6A–7B of the attached drawings, comprises a squeeze roller (7) able to roll over the sample under test and multifibre witness (4) located on the fixed plate (1) to exert a running or dynamic pressure of preset value thereon. The said roller (7) is engaged, freely rotating about its longitudinal axis, to two vertical plates (70) being fixed to said actuator (3), and is associated with a horizontal actuator (71) by which it is driven over the sample and multifibre witness (4) after being positioned thereon (see FIG. 6B).

According to a further embodiment, and as represented in the FIGS. 6A–7B of the attached drawings, a machine according to the invention comprises, in place of said squeeze roller, a skid (72) able to slide over the sample under test and multifibre witness (4) located on the plate (1) to exert a dynamic pressure and a rubbing action over the whole surface of the sample or the multifibre witness. The actuations of the skid (72) are of the same type as those of the squeeze roller (7), as far as the both vertical and horizontal movements are concerned.

With reference to the FIGS. 10A–11C of the attached drawings, a machine according to the invention may also be provided, in place of the said squeeze roller (7) or skid (72), with a disk able to rotatively slide over either the sample under test or the multifibre witness located on the fixed plate (1), to exert a rotary rubbing action onto the surface of the underlying material. The said disk (73) is associated with the vertical actuator (3) as previously described. The rotation of the disk (73) is determined by the actuator (71) which is engaged therewith via a rack (74) and pinion (75) transmission. The rack (74) is solid to the stem of the actuator (71); the pinion (75) is solid to the disk (73) on the side opposite to that intended for the contact of the materials to be tested. Accordingly, the motion of the stem of actuator (71) will cause the rotation of disk (73). Mounted between the disk (73) and the vertical actuator (3) is a pre-load device, with a vertical spring (76) disposed between the disk (73) and the end of actuator (3), the whole being located inside the pinion (75). The brackets (70), by which the disk (73)/actuator (71) assembly is associated with the actuator (3), exibit projecting edges (77) for retaining the material to be tested while the disk (73) rotates.

The liquids injecting and sucking means are not shown in FIGS. 6A, 6B, 8A, 8B, 10A and 10B for the sake of simplicity.

A process according to the invention, includes, subsequent to a step for the positioning of a multifibre witness (4) onto a support (1) and of a sample to be tested onto said witness, a step for the injection of one or more liquids (for example, water or organic solvents) through said support (1), prefereably in such a manner that each strip of the multifibre witness (4) will be acted upon by them.

The number of said holes (12) can however be different from that of strips (40–45) of the multifibre witness (4), the number of holes (12) being possibly lesser or higher than that of strips (40–45). In any case, the number of holes (12) formed on the plate (1) is more than one.

Preferably, as in the example shown in the drawings, such number coincides with that of strips (40–45) of the multifibre witness (4).

Advantageously, the same machine may also be used to perform tests on textile materials for accessing their ability to be dyed. In this case, the multifibre witness is not used: a sample of raw textile (not dyed) is positioned on the plate (1) and subject to compression as described above, while the liquids sucked through the discharge holes (13) of plate (1) exit from the same holes and, through the discharge circuit (6), collect into the vessels (60). These liquids can then be subjected to analysis (of a type well known to those skilled in the art) to check for substances of a nature which could endanger their ability of dyeing the material under test.

Practically, the construction details may vary in any equivalent way as far as the shape, dimensions, elements disposition, nature of the used materials are concerned, without nevertheless departing from the scope of the adopted solution idea and, thereby, remaining within the limits of the protection granted to the present patent for industrial invention.

The invention claimed is:

1. Machine for carrying out quick tests of color fastness on a textile sample with a multifiber witness or fabric standard, the machine comprising a plate supporting the textile sample, and means to compress the sample and multifiber witness or fabric standard on said plate, characterized in that said plate comprises a plurality of injection through holes associated with means for injecting one or more liquids there through for testing color fastness.

2. Machine according to claim 1 characterized in that said holes are lined up along a central line (t—t) of said plate and are equidistant to each other.

3. Machine according to claim 1 characterized in that a distance (d) between said holes corresponds to a center distance between strips of the multifiber witness or fabric standard.

4. Machine according to claim 1 characterized in that said plate further defines a plurality of discharge holes for discharging liquids, said discharge holes being located laterally to said injection holes.

5. Machine according to claim 4, characterized in that said discharge holes are lined up along two separate rows.

6. Machine according to claim 1 characterized in that each injection through hole includes a channel-shaped groove which also includes two corresponding lateral discharge holes.

7. Machine according to claim 5 characterized in that each row of discharge holes includes a channel-shaped groove.

8. Machine according to claim 1 characterized in that said means for compressing the sample and multifiber witness comprise a plate associated with a vertical actuator.

9. Machine according to claim 1 characterized in that said means for compressing the sample and multifiber witness comprise a roller associated with a vertical actuator and a horizontal actuator.

10. Machine according to claim 1 characterized in that said means for compressing the sample and multifiber witness comprise a skid associated with a vertical actuator and a horizontal actuator.

11. Machine according to claim 1 characterized in that said means for compressing the sample and multifiber witness comprise a rotary disk associated with a vertical actuator and a horizontal actuator.

12. Machine according to claim 1 characterized in that said plate is of square or rectangular shape.

13. Machine according to claim 1 characterized in that said plate is able to be heated and the operating temperature thereof can be controlled by relevant sensors.

14. A machine for color fastness testing a textile sample with a fabric standard, the machine comprising:
   a base plate for supporting the textile sample, and for also supporting the fabric standard, said base plate defining a plurality of through holes;
   a compressor connected to said base plate and compressing the sample and fabric standard on said base plate;
   an injection system injecting a liquid through said holes in said base plate and into the textile sample for color fastness testing.

* * * * *